United States Patent [19]
Rajala et al.

[11] Patent Number: 6,059,710
[45] Date of Patent: May 9, 2000

[54] PROCESS FOR CUTTING OF DISCRETE COMPONENTS OF A MULTI-COMPONENT WORKPIECE AND DEPOSITING THEM WITH REGISTRATION ON A MOVING WEB OF MATERIAL

[75] Inventors: Gregory John Rajala; Daniel James Oshefsky, both of Neenah; Thomas Raymond Holston, Appleton, all of Wis.

[73] Assignee: Kimberly-Clark Worldwide, Inc., Neenah, Wis.

[21] Appl. No.: 09/220,781

[22] Filed: Dec. 24, 1998

[51] Int. Cl.[7] .................................................... B31B 1/14
[52] U.S. Cl. ........................ 493/346; 493/362; 493/365; 493/369; 493/381; 493/938; 604/361; 604/365; 604/380; 604/387
[58] Field of Search ..................... 493/344–346, 493/362, 365, 369, 370, 379–381, 355, 937, 938, 464, 967; 604/358, 361, 365, 378, 380, 386, 387

[56] References Cited

U.S. PATENT DOCUMENTS

| | | | |
|---|---|---|---|
| Re. 29,365 | 8/1977 | Butler, Jr. .............................. | 242/58.3 |
| 2,254,217 | 9/1941 | Grupe ..................................... | 93/36.6 |
| 2,958,365 | 11/1960 | Molins et al. ........................... | 154/36 |
| 3,139,243 | 6/1964 | Warwick et al. ..................... | 242/156.2 |
| 3,146,152 | 8/1964 | Seragnoli ................................ | 156/519 |
| 3,516,891 | 6/1970 | Hubin ..................................... | 156/521 |
| 3,537,934 | 11/1970 | Munch ................................... | 156/364 |
| 3,582,437 | 6/1971 | Lenk ....................................... | 156/521 |
| 3,645,463 | 2/1972 | Helm ...................................... | 242/58.1 |
| 3,728,191 | 4/1973 | Wierzba et al. ........................ | 156/265 |
| 3,746,599 | 7/1973 | Peeters et al. .......................... | 156/505 |
| 3,758,367 | 9/1973 | Berg ....................................... | 156/519 |
| 3,835,756 | 9/1974 | Bosse ..................................... | 93/8 WA |
| 3,858,819 | 1/1975 | Butler, Jr. ............................... | 242/58.3 |
| 3,879,246 | 4/1975 | Walker ................................... | 156/265 |
| 3,886,031 | 5/1975 | Taitel ..................................... | 156/504 |
| 3,904,147 | 9/1975 | Taitel et al. .......................... | 242/156.2 |
| 3,918,655 | 11/1975 | Hillner et al. ......................... | 242/58.1 |
| 3,939,032 | 2/1976 | Taitel et al. ............................ | 156/505 |
| 3,957,570 | 5/1976 | Helm ...................................... | 156/519 |
| 3,963,557 | 6/1976 | Patterson ................................ | 156/519 |
| 3,995,791 | 12/1976 | Schoppee .............................. | 242/58.1 |
| 4,010,911 | 3/1977 | Heitmann .............................. | 242/58.4 |
| 4,021,293 | 5/1977 | Total ...................................... | 156/568 |
| 4,045,275 | 8/1977 | Stohlquist et al. .................... | 156/521 |
| 4,061,527 | 12/1977 | Traise .................................... | 156/519 |
| 4,083,737 | 4/1978 | Foote, Jr. et al. ..................... | 156/73.1 |
| 4,120,739 | 10/1978 | Peeters et al. ......................... | 156/506 |
| 4,157,934 | 6/1979 | Ryan et al. ............................ | 156/504 |
| 4,190,475 | 2/1980 | Marschke .............................. | 156/157 |
| 4,190,483 | 2/1980 | Ryan et al. ............................ | 156/504 |
| 4,261,782 | 4/1981 | Teed ...................................... | 156/361 |
| 4,262,855 | 4/1981 | Haag ...................................... | 242/58.1 |
| 4,309,236 | 1/1982 | Teed ...................................... | 156/164 |

(List continued on next page.)

*Primary Examiner*—Peter Vo
*Assistant Examiner*—Matthew Luby
*Attorney, Agent, or Firm*—Jerry F. Janssen

[57] ABSTRACT

The present invention provides a process for manufacturing a multi-component product comprising at least two components cut from moving webs of material, registering the components with respect to one another, and depositing the registered components on a web of moving material. The components have respective leading and trailing edges, a longitudinal center line, and a longitudinal center defined by a point midway on said longitudinal center line between said leading and trailing edges. The process comprises the steps of a) cutting the first workpiece components from a web of first material moving at first speed; b) transferring the cut first workpiece component to overlay a web of a second material moving at a second speed; c) cutting the second workpiece component from the second web while incorporating the overlying cut first workplace component wholly or partially within the cut boundaries of the second workpiece component; and d) transferring the cut and mated first and second workpiece components to a web of third material moving at a third speed. A process for making a multi-component sanitary napkin using the process of the invention is also disclosed.

31 Claims, 8 Drawing Sheets

U.S. PATENT DOCUMENTS

| | | | |
|---|---|---|---|
| 4,364,787 | 12/1982 | Radzins | 156/164 |
| 4,371,417 | 2/1983 | Frick et al. | 156/495 |
| 4,374,576 | 2/1983 | Ryan | 242/58.4 |
| 4,404,058 | 9/1983 | Marchini | 156/571 |
| 4,443,291 | 4/1984 | Reed | 156/504 |
| 4,455,190 | 6/1984 | Bianchetto et al. | 156/504 |
| 4,481,053 | 11/1984 | Tokuno et al. | 156/157 |
| 4,525,229 | 6/1985 | Suzuki et al. | 156/161 |
| 4,572,043 | 2/1986 | Bianco | 83/18 |
| 4,578,133 | 3/1986 | Oshefsky et al. | 156/164 |
| 4,610,751 | 9/1986 | Eschler | 156/517 |
| 4,617,082 | 10/1986 | Oshefsky et al. | 156/447 |
| 4,645,554 | 2/1987 | Wyser | 156/159 |
| 4,719,855 | 1/1988 | Cannon et al. | 101/426 |
| 4,726,876 | 2/1988 | Tomsovic, Jr. | 156/552 |
| 4,762,582 | 8/1988 | de Jonckheere | 156/164 |
| 4,767,487 | 8/1988 | Tomsovic, Jr. | 156/256 |
| 4,769,098 | 9/1988 | Cederholm et al. | 156/159 |
| 4,776,911 | 10/1988 | Uda et al. | 156/161 |
| 4,776,920 | 10/1988 | Ryan | 156/504 |
| 4,795,510 | 1/1989 | Wittrock et al. | 156/64 |
| 4,801,342 | 1/1989 | Wheeler et al. | 156/159 |
| 4,880,178 | 11/1989 | Goulette | 242/58.1 |
| 4,909,885 | 3/1990 | Swenson | 156/264 |
| 4,923,546 | 5/1990 | Wheeler et al. | 156/159 |
| 4,987,940 | 1/1991 | Straub et al. | 156/164 |
| 4,995,936 | 2/1991 | Cohn | 156/504 |
| 5,021,111 | 6/1991 | Swenson | 156/264 |
| 5,030,311 | 7/1991 | Michal et al. | 156/256 |
| 5,041,073 | 8/1991 | Eicker | 493/377 |
| 5,066,346 | 11/1991 | Long et al. | 156/157 |
| 5,091,039 | 2/1992 | Ujimoto et al. | 156/519 |
| 5,102,485 | 4/1992 | Keeler et al. | 156/256 |
| 5,102,486 | 4/1992 | Midgley et al. | 156/256 |
| 5,127,981 | 7/1992 | Straub et al. | 156/519 |
| 5,131,593 | 7/1992 | Siegfried et al. | 242/58.1 |
| 5,200,020 | 4/1993 | Collins et al. | 156/520 |
| 5,235,515 | 8/1993 | Ungpiyakul et al. | 364/469 |
| 5,244,530 | 9/1993 | Collins et al. | 156/519 |
| 5,261,996 | 11/1993 | Rossini | 156/521 |
| 5,286,543 | 2/1994 | Ungpiyakul et al. | 428/74 |
| 5,314,568 | 5/1994 | Ryan | 156/504 |
| 5,380,381 | 1/1995 | Otruba | 156/64 |
| 5,383,988 | 1/1995 | Herrmann et al. | 156/64 |
| 5,407,507 | 4/1995 | Ball | 156/163 |
| 5,407,513 | 4/1995 | Hayden et al. | 156/265 |
| 5,413,651 | 5/1995 | Otruba | 156/64 |
| 5,415,716 | 5/1995 | Kendall | 156/256 |
| 5,492,591 | 2/1996 | Herrmann et al. | 156/538 |
| 5,549,783 | 8/1996 | Schroeder et al. | 156/542 |
| 5,552,007 | 9/1996 | Rajala et al. | 156/164 |
| 5,556,504 | 9/1996 | Rajala et al. | 156/519 |
| 5,562,793 | 10/1996 | Menard | 156/263 |
| 5,580,411 | 12/1996 | Nease et al. | 156/260 |
| 5,582,668 | 12/1996 | Kling | 156/161 |
| 5,591,297 | 1/1997 | Ahr | 156/521 |
| 5,595,335 | 1/1997 | Borel | 226/42 |
| 5,597,437 | 1/1997 | Lange et al. | 156/260 |
| 5,643,396 | 7/1997 | Rajala et al. | 156/361 |
| 5,659,538 | 8/1997 | Stuebe et al. | 364/469.02 |
| 5,660,657 | 8/1997 | Rajala et al. | 156/64 |
| 5,679,195 | 10/1997 | O'Dwyer et al. | 156/159 |
| 5,693,165 | 12/1997 | Schmitz | 156/164 |
| 5,695,846 | 12/1997 | Lange et al. | 428/98 |
| 5,702,551 | 12/1997 | Huber et al. | 156/73.1 |
| 5,705,013 | 1/1998 | Nease et al. | 156/260 |
| 5,716,478 | 2/1998 | Boothe et al. | 156/302 |

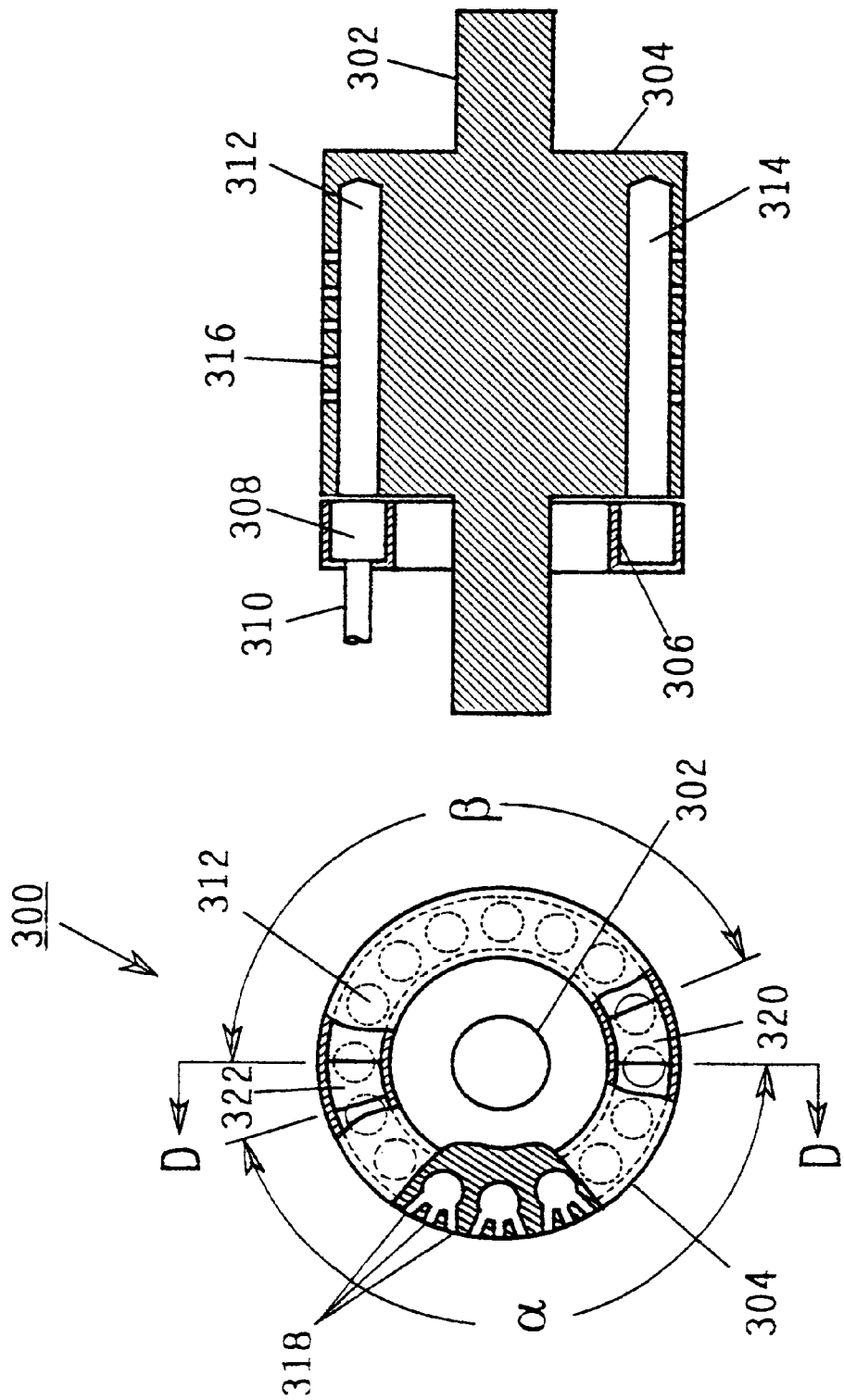

PROCESS FOR CUTTING OF DISCRETE COMPONENTS OF A MULTI-COMPONENT WORKPIECE AND DEPOSITING THEM WITH REGISTRATION ON A MOVING WEB OF MATERIAL

FIELD OF THE INVENTION

The present invention relates to a method for cutting parts of a workpiece traveling at different speeds relative to one another and applying the parts to a moving web of material. More particularly, the invention concerns a method for cutting parts from at least two webs of moving material moving at different speeds and depositing the parts with controllable registration on a third continuously moving web of material.

BACKGROUND OF THE INVENTION

Articles such as infant diapers, adult continence garments, feminine napkins and the like have been manufactured generally by processes where parts or components of the article are deposited on a continuously moving product web. Often, the speed with which the parts or components are produced and fed into the process is not the same as the speed of advance of the product web itself. In such cases, the speed of production and/or deposition of the component parts on the moving web must be varied to match the speed of the product web to properly match the parts to the moving web without adversely affecting the process or finished article.

Several methods for changing the speed of a part or component of material for deposition on a continuously moving web are known in the art. One method employs rollers segmented into sections which are inwardly and outwardly moveable in a direction radial to their direction of rotation. As the roller rotates, the segments are driven by cam actuating or gearing means to move inwardly and outwardly changing the linear surface speed of the roller segments as the roller rotates through each revolution.

Another method utilizes festoons to reduce the speed of the moving web to which the parts or components are to be applied. The continuously moving web is temporarily slowed to the speed of the component parts to be deposited. with the excess portion of the continuously moving web gathering in festoons. While the continuously moving web is slowed to match the speed of the component parts, the parts are transferred to the web and the speed of the web is then accelerated to gather the festoons prior to the next cycle.

Another method is the so-called "slip gap" method in which the parts or components are cut from a web of material moving at a slower speed than the product web. As the component parts are cut from the first web of material, they are held to either the anvil roller or the cutter roller by means of vacuum. As the pieces pass tangentially to the continuously moving product web which is moving at a different speed, the parts or components slip temporarily until they are vacuum transferred to the continuously moving product web.

These known methods of transferring component parts, moving at one speed, to a continuously moving web moving at a different speed, do not address the problem of insuring careful registration of the deposited component parts on the continuously moving web. The problem is exacerbated when the need exists for depositing two or more components, one on top of the other on the continuously moving web while insuring careful registration of one component to the other, or to the moving web.

There remains a need for an efficient process for depositing workpiece components moving at different web speeds on a substrate web which process insures accurate registration of the parts with respect to one another.

SUMMARY OF THE INVENTION

In accordance with the present invention, there is provided a process for manufacturing a multi-component product comprising at least two components cut from moving webs of material, registering the components with respect to one another, and depositing the registered components on a web of moving material. The components have respective leading and trailing edges, a longitudinal center line, and a longitudinal center defined by a point midway on said longitudinal center line between said leading and trailing edges. The process comprises the steps of a) cutting the first workpiece components from a web of first material moving at first speed: b) transferring the cut first workpiece component to overlay a web of a second material moving at a second speed; c) cutting the second workpiece component from the second web while incorporating the overlying cut first workplace component wholly or partially within the cut boundaries of the second workpiece component; and d) transferring the cut and mated first and second workpiece components to a web of third material moving at a third speed.

In a preferred embodiment, the present invention provides a method of manufacturing a multi-component absorbent personal hygiene article comprising a cover layer, a distribution or wicking component layer, a fluid transfer delay component layer, and an absorbent layer, and a barrier or backing layer, with the distribution, fluid retaining and absorbent layers being of different length and positionally registered with respect to one another on the backing layer.

BRIEF DESCRIPTION OF THE DRAWING FIGURES

FIG. 12 shows an end-view of a center commutator vacuum system.

FIG. 13 shows a cross sectional view of the commutator of FIG. 12 taken along cut line D—D.

Figure 1:
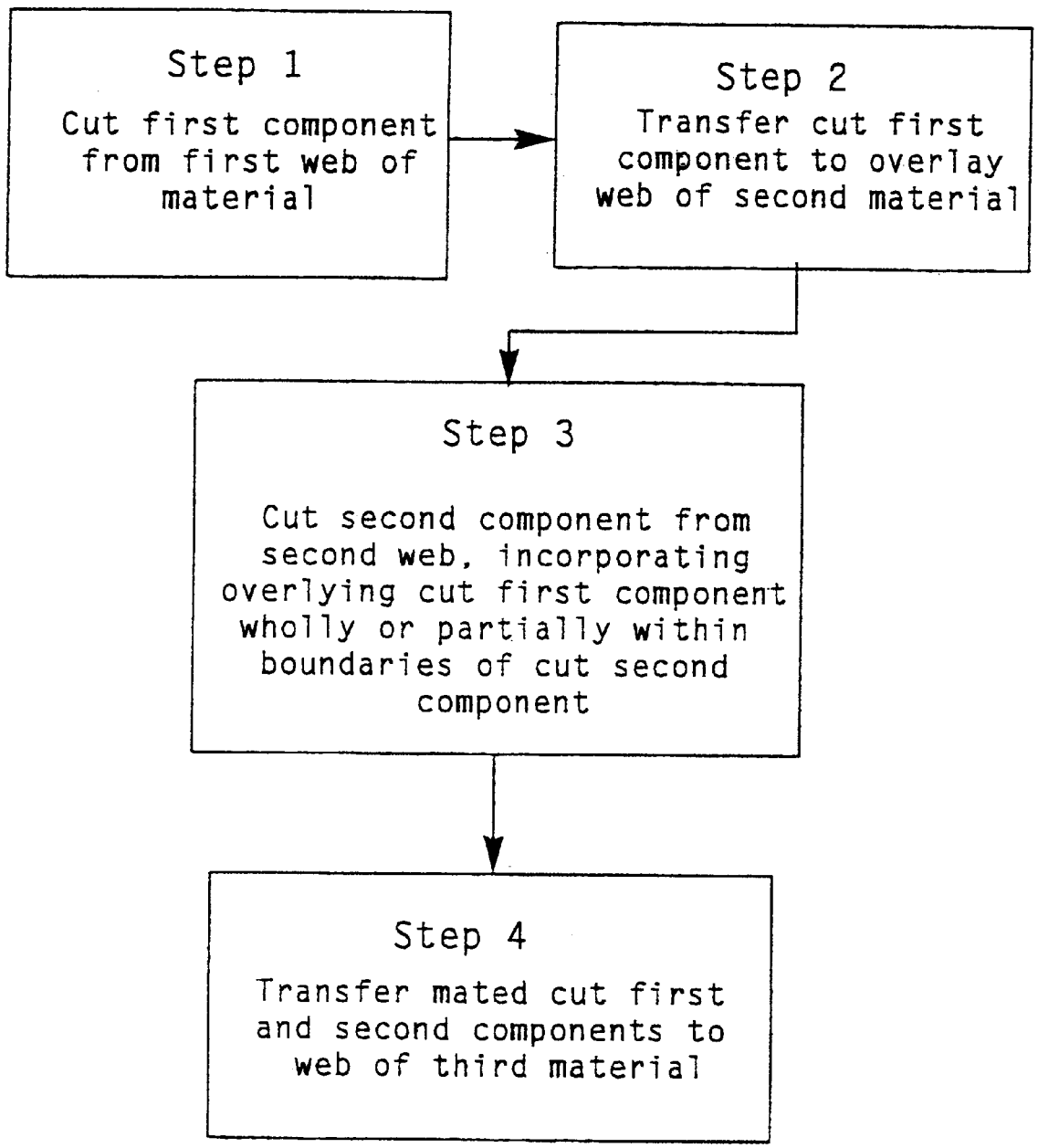
FIG. 1 is a representation of the steps of the general process of the present invention.
Figure 2:
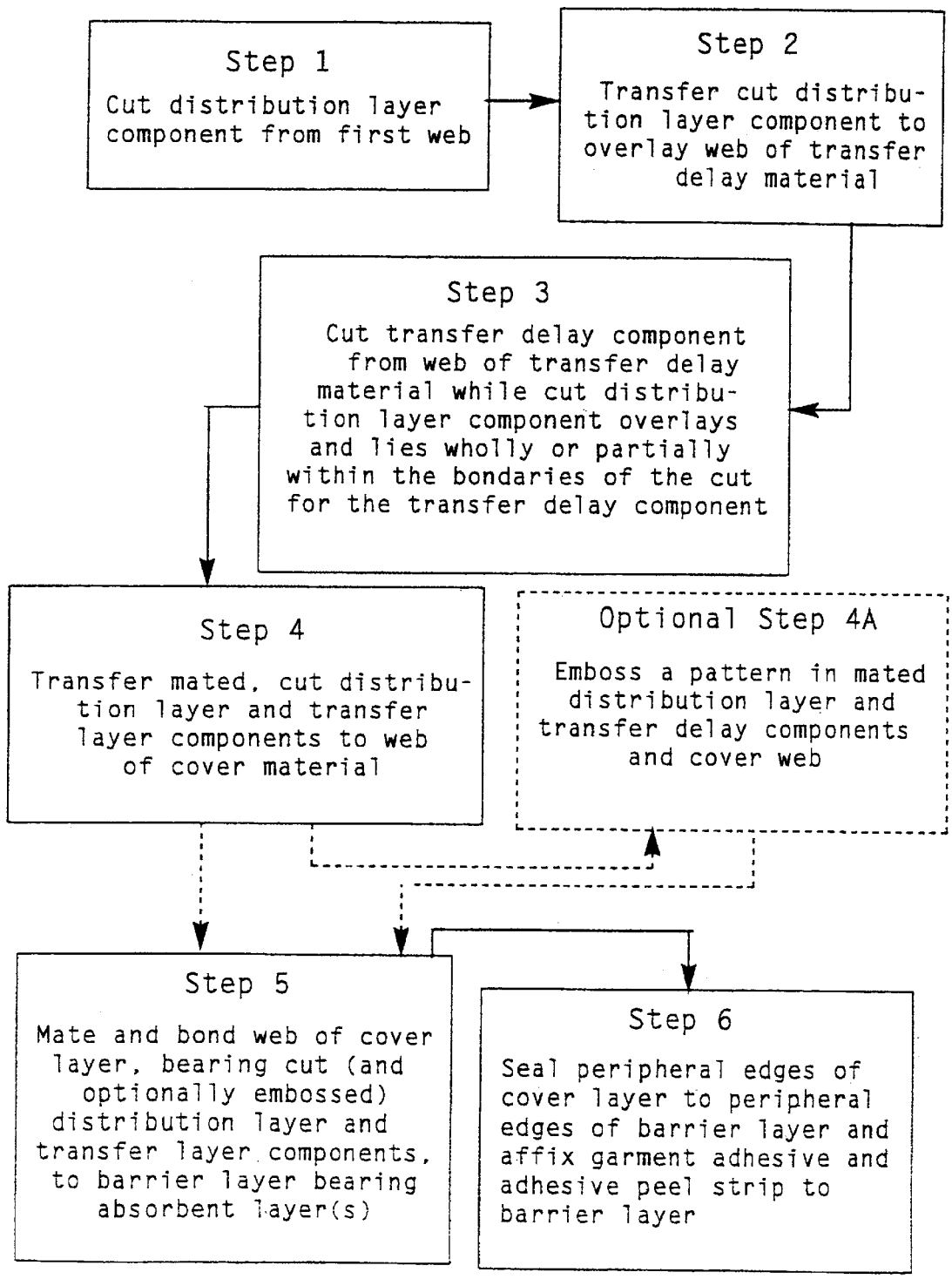
FIG. 2 is a representation of the steps of manufacturing a sanitary napkin utilizing the process of the present invention.

The invention is not limited in its application to the details or arrangement of the machine components or process steps set forth in the following description or illustrated in the drawings. The invention is capable of other embodiments or of being practiced or carried out in various other ways. Also, it is to be understood that the terminology and phraseology employed herein is for purpose of description and illustration and should not be regarded as limiting. Like reference numerals in the drawing figures are used to indicate like components.

DETAILED DESCRIPTION OF THE ILLUSTRATED EMBODIMENTS

Figure 3:
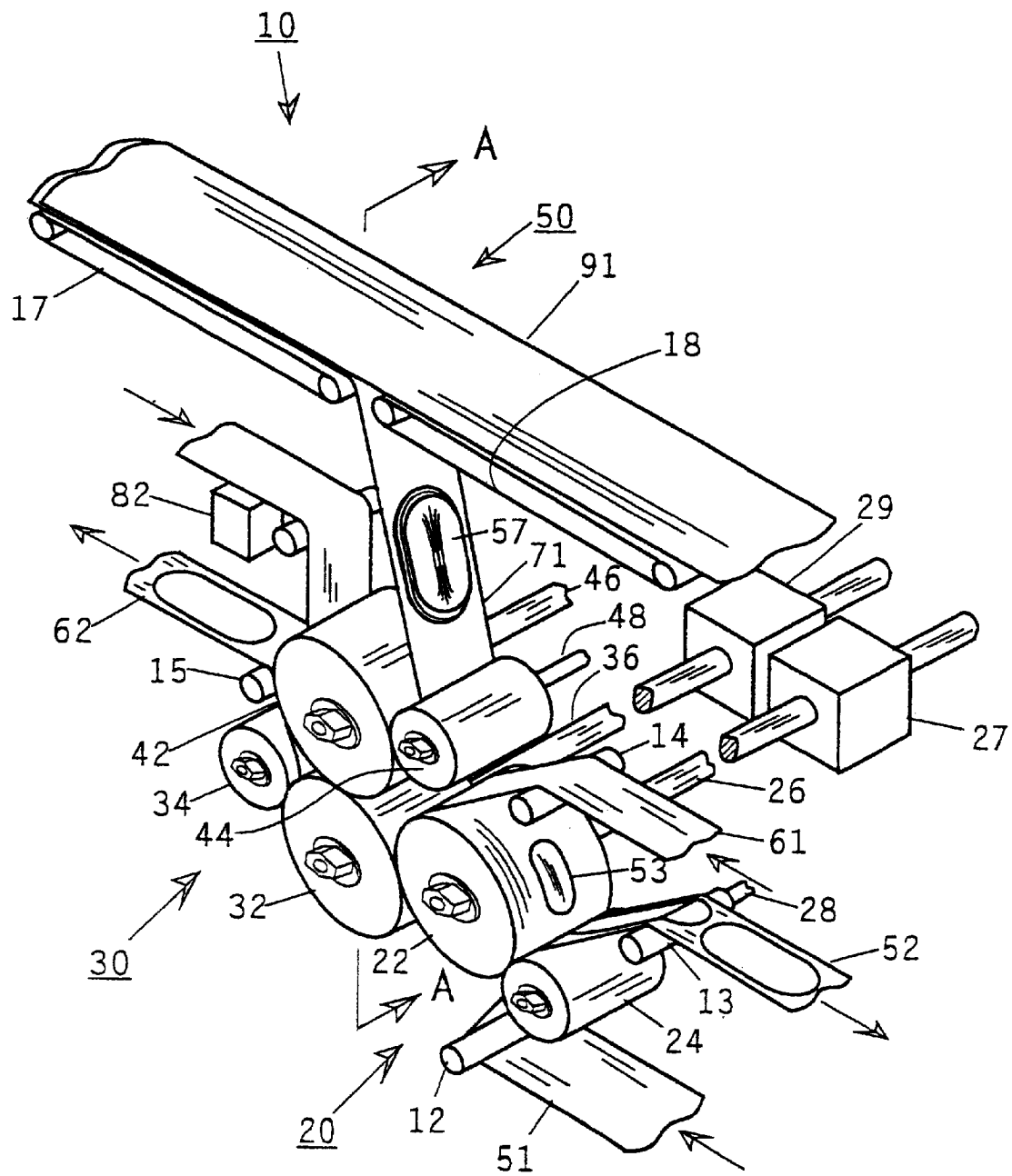
FIG. 3 shows, in a perspective view, a schematic representation of one embodiment of a machine for practicing the process of the present invention.

One embodiment of a machine for carrying out the process of the present invention is represented in FIG. 3 which shows schematically a machine for depositing two components of differing lengths, cut from webs of material moving at different speeds, registered with respect to one another, and depositing them on a third web moving at a third velocity. Since the two components have different lengths, the webs from which each is cut and the apparatus for cutting each from its web, must move at different speeds. The machine of the invention provides for the mating and registration of the two components, as well as for the deposition of the mated components onto a third web which is moving at a speed different from that of either of the two webs from which the components were cut.

Figure 4:
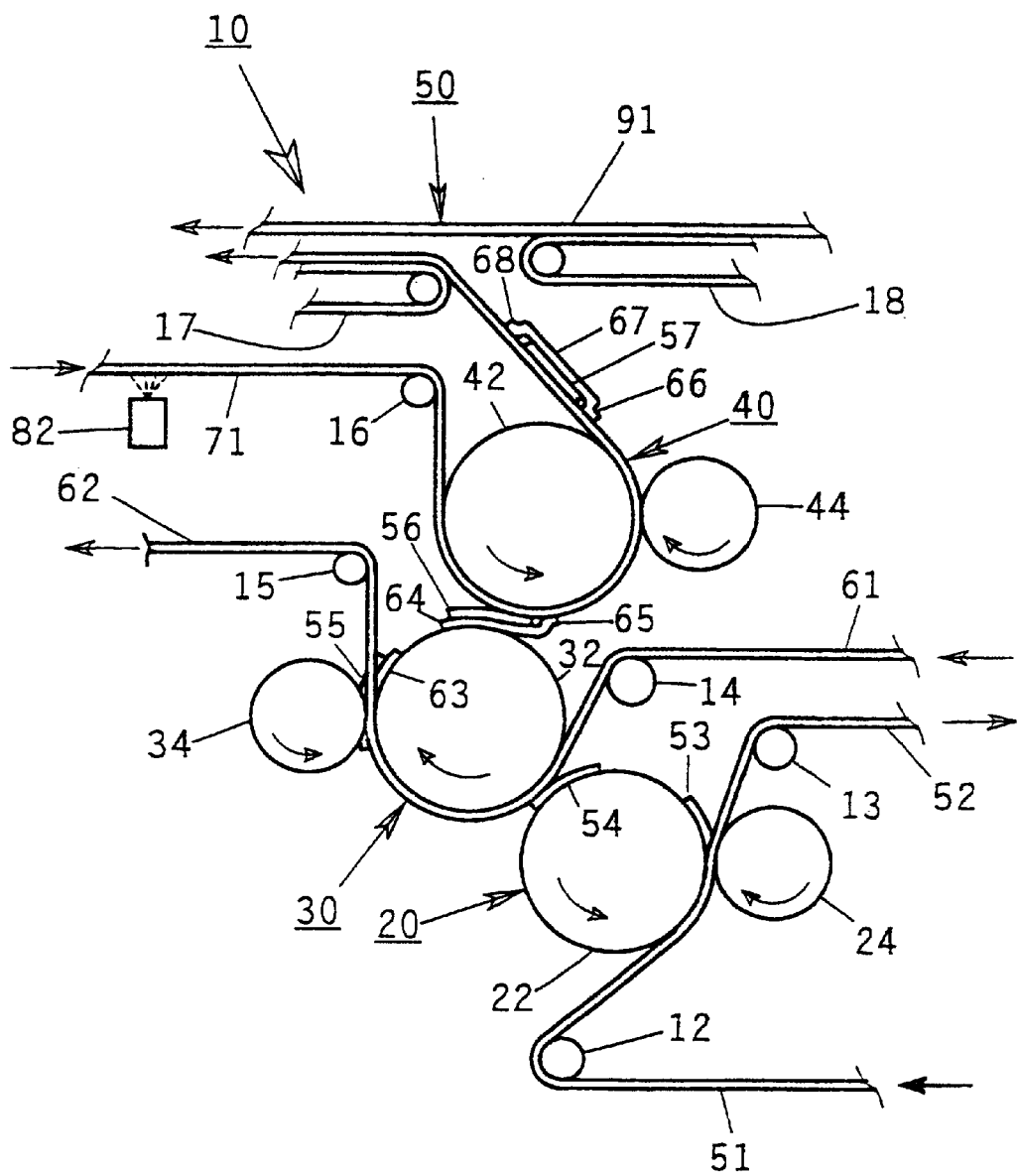
FIG. 4 shows the components and product webs moving through the machine of FIG. 3 in a side view taken along cut line A—A of FIG. 3.

Referring to FIGS. 3 and 4, the machine 10 comprises as its main components, a first component die cutting and transfer apparatus 20, a second component die cutting and transfer apparatus 30, an embossing apparatus 40, and a main product web transport apparatus 50. Embossing roller 42 and its associated embossing anvil roller 44 are driven at a constant speed equal to the machine line shaft speed and the speed of the product web 91, measured in terms of product per minute. First 22 and second 32 component die cut and transfer rollers and their respective cutter anvil rollers 24 and 34 are driven at constant speed.

Referring to FIGS. 3 and 4, a web 51 of a first material is delivered under slight tension to roller 12. The material then passes between first component die cut and transfer roller 22 and die cut anvil roller 24 to cut the web 51 of first material into component pieces 53 having the desired shape and dimensions.

Figure 5:
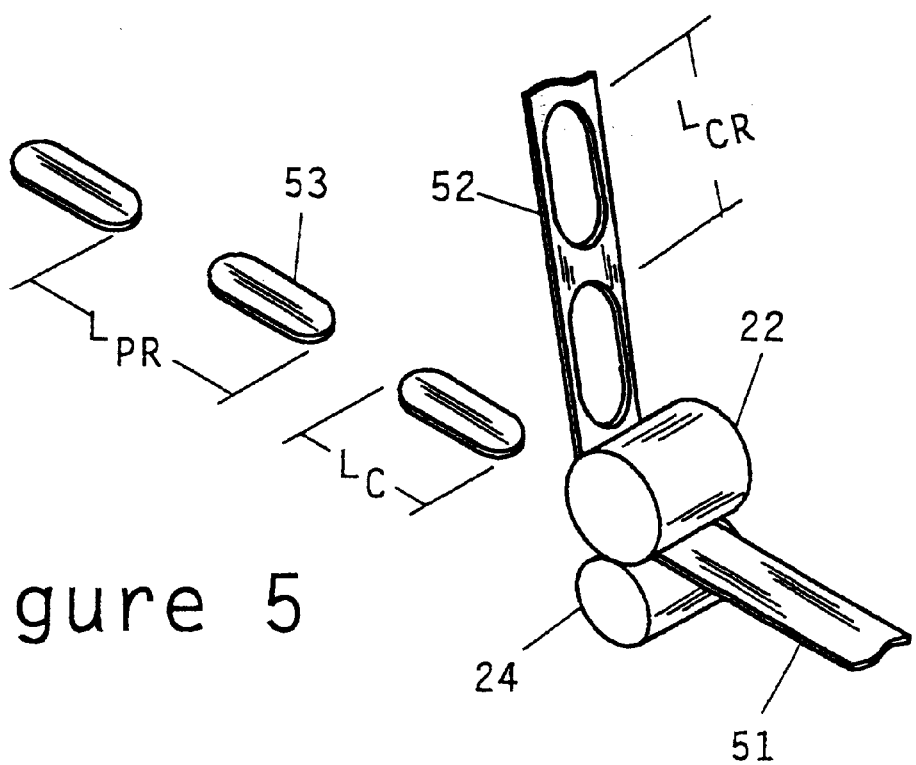
FIG. 5 shows a schematic representation of a die cut and anvil roller assembly for cutting a web of material by the "ladder cut" method.
Figure 6:
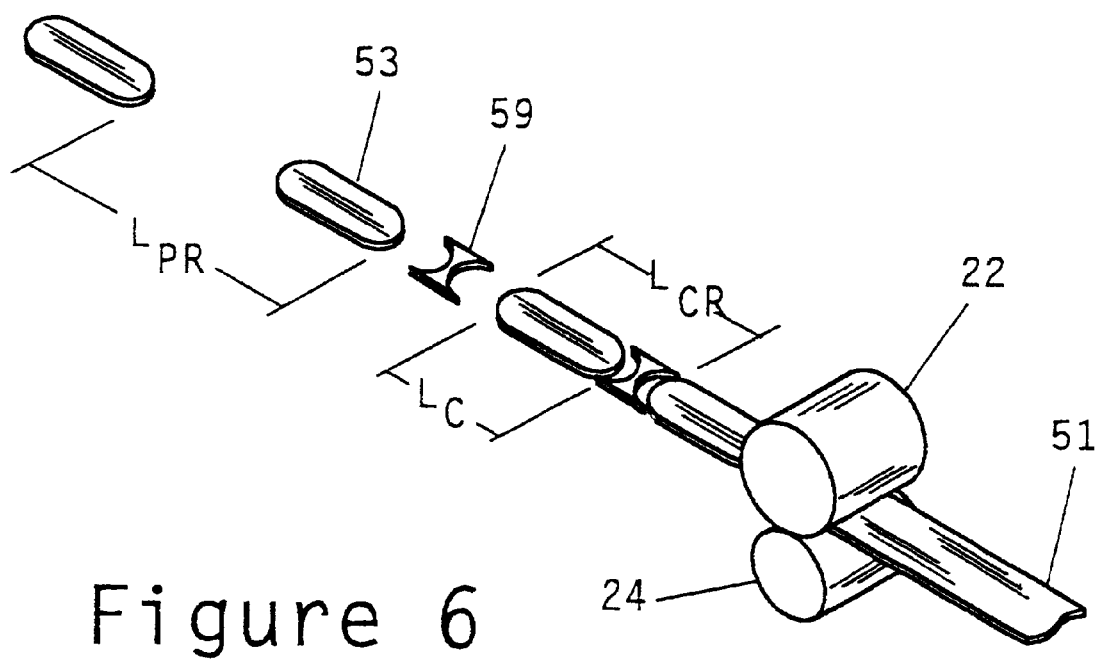
FIG. 6 shows a schematic representation of a die cut and anvil roller assembly for cutting a web of material by the "butterfly cut" method.

The "cookie cutter" blade on die cut and transfer roller 22 may be configured to cut component pieces by either a "ladder cut" method or a "butterfly cut" method as shown in FIGS. 5 and 6, respectively. The ladder cut method is depicted in a generalized manner in FIG. 5, where an advancing web 51 of material passes between die cut and transfer roller 22 and anvil roller 24. The scrap "ladder" 52 of cut web is shown moving up and away from the die cut and anvil rollers. A cut first component piece 53 is shown moving along the process stream away from the rollers. The lengths of the cut component pieces 53 are indicated in FIGS. 5 and 6 by the dimension $L_C$. The component repeat length, i.e. the distance between the leading edge of one cut component and the leading edge of the next following cut component, is indicated as $L_{CR}$ and the product repeat length, i.e. the distance between the leading edge of one completed product and the leading edge of the next following product in the process stream, is indicated at $L_{PR}$ which may or may not be the same as the component repeat lengths.

While shown as pieces having parallel sides and semi-circular ends, the component pieces 53, cut by the ladder cut method, may be of any desired shape. Since the web 51 of material in the ladder cut method is of a width greater than the width of the cut component pieces, there is a region of scrap in the ladder 52 along the sides of each component piece. Likewise, a scrap region of length $L_{CR}$–$L_C$ exists between successive component pieces. As a result, the component pieces 53 may be cut in any desired shape by the ladder cut method, as for example circular, elliptical, "dog-bone" shape, serrated, etc. While possessing the advantage of permitting the component pieces to be cut in any desired shape, the ladder cut method suffers, however, from the disadvantage of having more scrap than the butterfly cut method, which is depicted in FIG. 6.

In FIG. 6, an advancing web 51 of material is shown as passing between die cut roller 22 and anvil roller 24 to produce the component pieces 53 cut by the butterfly method. The scrap pieces 59 are smaller than those derived from the ladder cut method. The component length, component repeat length, and product repeat length, are indicated as $L_C$, $L_{CR}$, and $L_{PR}$, respectively, as in FIG. 5.

Since, in the butterfly cut method, the web of material 51 is the same width as the final cut component pieces 53, there is less scrap but the cut pieces are constrained to have the parallel sides of the web 51. However, in an alternative embodiment, the side edges of the advancing web of material to be cut by the butterfly method may be previously cut so that the sides of the web have a repeating pattern of any desired shape. It is a simple matter to match the cutting frequency in the die cut roller to the frequency of repetition of the side-cut pattern in the web to produce component pieces cut by the butterfly cut method, but having shaped side edges. This alternative adds, however, to the cost and complexity of the process and the option of cutting component pieces by the butterfly method from a web having parallel sides is preferred.

The butterfly cut method is also preferred in those instances where the web of material to be cut into component pieces is costly, and the amount of scrap generated by the cutting process is to be minimized.

Referring again to FIGS. 3 and 4, the figures show the first component web 51 being cut into component pieces by the ladder cut method, but as mentioned above, either the ladder cut or butterfly cut method may be used. During the step of cutting the first discrete components 53 from web 51, die cut and transfer roller 22 and its associated cutter anvil roller 24 move at the speed of advancing web 51. As the component is cut from the web, its leading edge is held to the surface of the die cut and transfer roller 22 by vacuum means internal to the roller 22, as well as by the natural tendency of the cut component to remain in the "cookie cutter" blade. This tendency of the cut component to remain in the cutter blade is used to advantage on the die cut transfer rollers as will be discussed below.

Once the component 53 is completely severed from the web 51, the component is transferred to web 61. A unique feature of the machine and process of the present invention is the transfer of the first cut component from a first die cut roller directly to a second die cut roller. By this means, the machine of the invention permits the cutting of components from the second web of material while the components already cut from the first web overly the second web of material. To assist in the transfer of the first cut component from the first die cut transfer roller, the vacuum internal to the first die cut roller is turned off and vacuum on the second die cut transfer roller is turned on. In addition, if needed or desired, the mechanism controlling internal air pressure in the first die cut transfer roller can be set at a pressure slightly above ambient to push the cut component out of the cookie cutter blade at the appropriate point in the rotation of the roller. This is done by appropriate placement of vacuum slugs in a side commutator vacuum system more fully described below.

A web of second material 61 passes over roller 14 and enters the slight gap between die cut and transfer roller 32 and anvil roller 34 and receives a previously-cut first component, shown as 54 in FIG. 4. Cut first component 54, as it comes away from the first web 51 overlays, or lies on top of the web of second material 61. The terms "overlay" or "lie on top of" with respect to cut first components 54 mean the web of second material lies between the cut first component and the die cut and transfer roller 32.

Vacuum means, internal to die cut and transfer roller 32 holds both the web of second material and the cut first component 54 to roller 32 in the manner described below as roller 32 turns. As the second web of material 61 and the overlying first component 54 travel with die cut and transfer roller 32, they enter the gap between die cut roller 32 and anvil roller 34. A cut is made in the second web 61 of material as the overlying cut first component, shown as 55 passes through the cutter gap between rollers 32 and 34. The cut in the web of second material 61 may produce a cut second component piece which is of the same overall dimensions as the cut first components, or of different overall dimensions, either larger or smaller. The shape and dimensions of the cut second component 63 will, of course be controlled only by the shape and dimensions of the die cut blade on the face of roller 32. Since the cut in the second web of material is made as both the second web 61 and the cut first component 55 pass between the die cut roller 32 and its associated anvil roller 34, a number of resulting cuts in the overlying first component may or may not be made, depending on the relative registration of the cut first component with the second component die cutter, and the shape and dimensions of the second die cut roller blade.

The various situations which can result are best seen by reference to Table 1 which presents a matrix of the possibilities. In Table 1, the term "longitudinal center" of A workpiece component means the point on a center line running through the workpiece in the direction of the web or workpiece flow through the machine, mid-way between the leading and trailing edges of the workpiece. Similarly, the term "longitudinal center" of the cutter blade on the second cutter roller means a point on a center line running through the cutter blade in the direction of the web or workpiece flow through the machine, mid-way between the leading and trailing edges of the blade. The terms "leading edge" and "trailing edge," when referring to workpiece components or the second web cutter blade, mean, respectively, the up-stream and down-stream edges with regard to workpiece flow through the machine.

It is to be understood that the matrix of possibilities presented in Table 1 does not treat of the consequences on the relative widths and lateral placement of the two components. These are affected only by the predetermined parameters of 1) the widths of the first component and second component webs, 2) the width of the first and second component cutting blades on the respective cutting rollers, and 3) the lateral placement of the two webs with regard to the cutter rollers as the webs pass through the machine.

TABLE 1

Effect on First Component by Die Cut Blade on the Face of Second Die Cut and Transfer Roller

| Placement and Length of First Component with Respect to Second Component | Length of first cut component is less than length of second cut component ($L_{C1} < L_{C2}$) | Length of first cut component is greater than length of second cut component ($L_{C1} > L_{C2}$) |
| --- | --- | --- |
| Longitudinal centers of first cut component and second component coincide when cut is made in second web | First component is longitudinally centered on second component; no cut is made in either end of first component | Leading and trailing edges of first component are cut again by second web cutter blade so that first component is the same size as the second component |
| Longitudinal centers of first cut component and second component do not coincide when cut is made in second web; leading edge of first component does not lead leading edge of die cut blade for second component | First component is longitudinally off-center on second component; no cut is made in either end of first component | Trailing edge of first component is trimmed so that first and second components are of equal length |
| Longitudinal centers of first cut component and second component do not coincide when cut is made in second web; leading edge of first component leads leading edge of die cut blade for second component | Leading edge of first component is trimmed to match the leading edge of the second component | a) If off-set in longitudinal centers of first component and die cut blade is less than to $L_{C1}-L_{C2}$, both the leading and trailing edges of first component are cut again by second web cutter blade so that first component is the same size as the second component; b) if off-set in longitudinal centers of first component and die cut blade is greater than to $L_{C1}-L_{C2}$, the leading edge of first component is cut again by second web cutter blade |
| Longitudinal centers of first cut component and second component do not coincide when cut is made in second web; trailing edge of first component trails trailing edge of die cut blade for second component | Trailing edge of first component is trimmed to match the trailing edge of the second component | a) If off-set in longitudinal centers of first component and die cut blade is less than to $L_{C1}-L_{C2}$, both the leading and trailing edges of first component are cut again by second web cutter blade so that first component is the same size as the second component; b) if off-set in longitudinal centers of first component and die cut blade is greater than to $L_{C1}-L_{C2}$, the trailing edge of first component is cut again by second web cutter blade |

It is preferred that the cutter blades are centered longitudinally with respect to the first and second webs as they pass through the machine. It is particularly preferred that the first component cutter blade is narrower that the second so that the width of the cut first component is less than that of the second cut component. Likewise, it is preferred that the relative sizes of the first and second cut workpiece components and their relative registration is such that the leading edge of the second cut component leads that of the leading edge of the first cut component. In a particularly preferred embodiment, the first cut component is both narrower and shorter than the second cut component, and is centered with respect to the second component. In this way a peripheral band of the second cut component extends beyond the periphery of the first cut component around the entirety of both components. In another particularly preferred embodiment, the first and second component cutter blades are chosen to have sizes and shapes with respect to one another, and the registration of the first and second cut components such that the peripheral band of the second component extending beyond the periphery of the first cut component is uniform in width around the entirety of the two components.

By indexing the die cut rollers 22 and 32 with respect to one another, the first component piece can be controllably registered with respect to the second component piece so that the first piece is centered on the second, or, in such a manner that the leading end of the advancing first piece leads or trails the leading edge of the second piece by any desired amount. This indexing is achieved in a manner well understood in the mechanical arts by interposing between the machine line shaft and the shaft driving either or both die cut roller 22 or 32 a phase shift differential of the type manufactured by Fairchild Industrial Products Co., 1501 Fairchild Drive, Winston-Salem, N.C., USA under the trade name "Specon®." This permits adjusting the phase angle between die cut rollers 22 and 32 to advance or delay the cutting of one of the components with respect to the other.

Returning to the description of the flow of the webs and workpiece components through the machine as depicted in FIGS. 3 and 4, once the second component is completely severed from the web of second material 61, the stacked first and second components are transferred to web 71.

The stacked first and second cut components, held to the surface of the die cut and transfer roller 32 by vacuum means internal to the roller, are moved into the gap between die cut and transfer roller 32 and an optional embossing roller 42. A web of third material 71, under slight tension, is shown in FIG. 4 entering the machine over roller 16 after having received an application of adhesive from adhesive applicator 82. The adhesive employed is chosen for its suitability to the materials making up the first, second and third webs of material after the manner well known in the diaper and feminine care article art.

The stacked cut first and second components are pressed to the web of third material 71 in the gap between roller 32 and roller 42. As shown in FIG. 4. stacked first component 56 and second component 64 are shown in the gap between the two rollers. The surface of first component 56 next adjacent the web of third material 71 is held to web 71 by the previously-applied adhesive, as is the edge of the larger second component 64 which protrudes around the first component 56. As indicated in FIG. 4, the leading edge 65 of second component 64 is shown adhered to the web 71 of third material as the stacked pair of components are shown leaving the gap between rollers 32 and 42.

The stacked cut, first and second workpiece components next pass through the gap between optional embossing roller 42 and embossing roller anvil 44 and a pattern is impressed upon the two stacked components and the web of third material 71. Simultaneously, the pressing action of the two rollers forms a complete seal between web of third material 71 and the edge of the cut second component which protrudes outwardly from the edge of the cut first component. This action forms a "sandwich" in which the smaller cut first component is sealed between the cut second component and the web of third material.

The web of third material 71, bearing the sealed "sandwich" of first and second components is then received on conveyor belt 17 where the web of third material and components are mated to advancing product web 91 which may or may not bear additional product components.

The embossing step is optional and, if not desired, can be eliminated by simply making the face of roller 42 smooth rather than having a raised embossing pattern.

Third web 71, now bearing the first and second cut workpiece components (shown as element 57 in FIG. 3) bonded to the web surface, are next received on conveyor belt 17 where the third web and components are mated with a fourth web 91 bearing additional components of the product, assembled up-stream from the machine assembly shown in FIG. 3. As the third web 71 and fourth web 91, each bearing their respective product workplace components move downstream, additional operations, as needed or desired are performed on both webs. These operations may include, for example, bonding the third and fourth webs to one another by conventional means known in the art, and adding addition product components to the upper surface of fourth web 91.

Figures 10, 11:
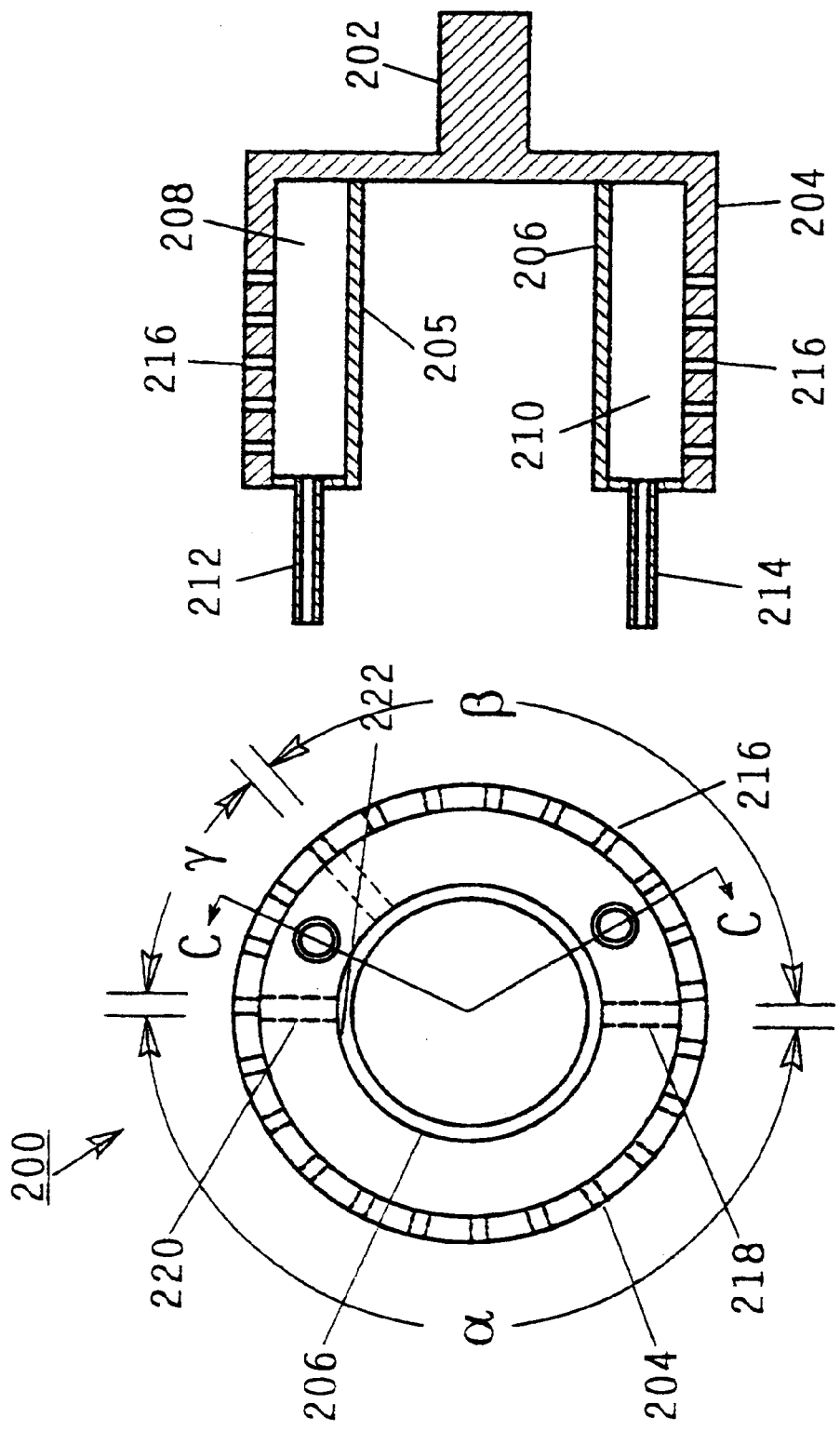
FIG. 10 is an end view of a side commutator vacuum system.
FIG. 11 shows a cross sectional view of the commutator of FIG. 10 taken along cut line C—C.

The vacuum systems employed for holding cut workpiece components to the die cut and transfer rollers employ conventional vacuum systems well known in the art. These are illustrated generally in FIGS. 10–13. FIG. 10 shows an end-view of a so-called "side-commutator" vacuum system 200. FIG. 11 shows the vacuum system of FIG. 10 in a cross-section taken along cut line C—C.

Referring to FIG. 11, the system comprises a stationary commutator made up of two sections 205 and 206. The upper section in FIG. 11 comprises a chamber 208 and tube 212 through which high vacuum is introduced into chamber 208. The lower section 206 of the commutator in FIG. 11 comprises a chamber 210 into which low vacuum is introduced through tube 214.

Referring to FIG. 10, baffles 218, 220, and 222 are shown which divide the commutator into three chambers: a chamber into which no vacuum is introduced, a chamber of low vacuum, and a chamber of high vacuum. These chambers correspond to the arcs α,β, and γ, respectively. Unlike the side-commutator system described below, in the center commutator system, vacuum is maintained in the low and high vacuum chambers at all times, while the radial holes 216 in concentric rotor 204 move past each chamber. In this way, no vacuum, low vacuum, or high vacuum is introduced to the outer surface of the rotor 204 sequentially as the rotor 204 turns through each revolution on shaft 202.

The lengths of arcs α, β, and γ, are determined, and can be changed by, movement of the baffles 218, 220, and 222. The center-commutator system 200, with its capability of having zones of non vacuum, low vacuum, and high vacuum, is well adapted for rollers in the machine of the invention where it is necessary to turn on and turn off vacuum, and to have regions of high vacuum as, for example in the die cut and transfer roller 32 where both the first and second cut workpiece components need to be held to the surface of the roller.

FIG. 12 shows an end-view of a so-called "center commutator" vacuum system 300. In the figure, the vacuum system comprises a stationary commutator 306 and rotor 304. The rotor 304 has a series of tubular holes 312 and 314 drilled into it, parallel to the axis of rotation of the rotor 304. Holes 316, and 318 drilled radially in the rotor 304 connect the axial tubes or holes 312 and 314 to the outer surface of the rotor. Vacuum is introduced into the commutator through entry tube 310 in the zone between the vacuum slugs 320 and 322.

Referring to FIG. 12, vacuum slugs 320 and 322 block the connection of the commutator 306 to the axial tubes 312 and 314 in the rotor 304 during a fraction of each rotation of the rotor. Thus, vacuum is introduced into tubes 312 and 314 of the rotor only during that portion of each rotation of the rotor designated by the arc β when no vacuum slug is interposed between the commutator 306 and the rotor 304. The moveable vacuum slugs 320 and 322 determine the ends of vacuum zone defined by the arc β. The lengths of the arcs α and β can be adjusted by appropriate placement of the vacuum slugs. The side-commutator system 300 is well adapted for rollers in the machine of the invention where firmer support of the roller is required as, for example in the die cut roller 22.

While there has been shown and illustrated one embodiment of the machine of the invention for depositing and registering two workpiece components of differing length on one another and subsequently onto a constantly moving web of material, it will be readily seen by one of ordinary skill in the mechanical arts that the machine can be modified to introduce and register third, fourth, fifth, etc. workpiece components by simply introducing additional components of type illustrated in FIG. 3 and described above into the machine either up-stream or down-stream in the process from the corresponding elements shown. In this manner, the machine of the present invention provides an efficient and cost-effective device for manufacturing multi-component articles of manufacture where there is a need to "stack" up and register workpiece components and subsequently deposit them with registration on a constantly moving web.

Having thus described the machine and process for cutting and stacking, with registration, two workpiece components of different lengths and depositing them on a constantly moving web, the following example illustrates the use of the process and machine of the invention for the manufacture of a multi-layer feminine hygiene napkin.

EXAMPLE

Figure 7:
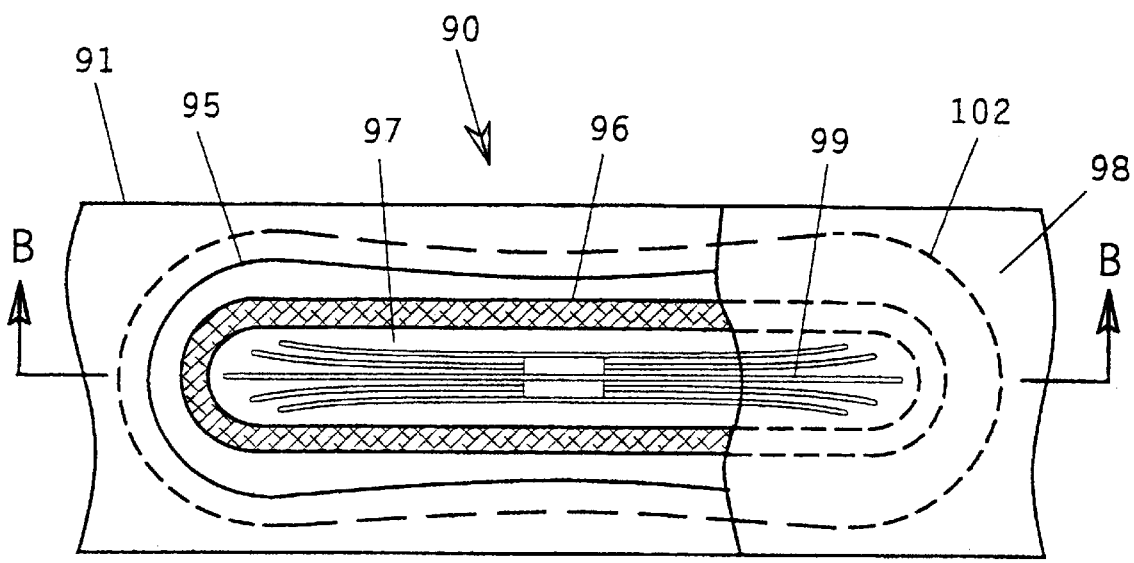
FIG. 7 shows a partially cut-away plan view of a so-called "mini" sanitary napkin produced by the machine and process of the present invention.
Figure 8:
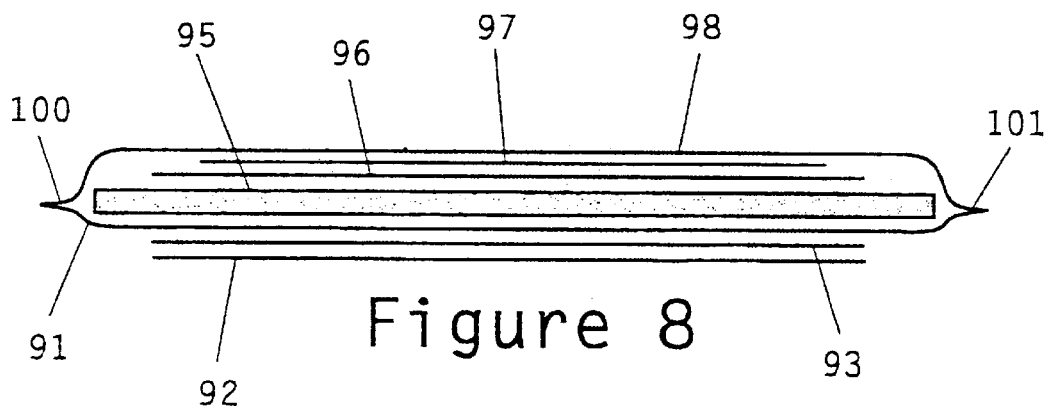
FIG. 8 shows a cut-away side view of the sanitary napkin of FIG. 8 taken along cut line B—B of FIG. 7.

A so-called ultra-thin or "mini" napkin, suitable for use by a woman during days of light menstrual flow, is depicted schematically in plan view in FIG. 7 and in schematic cross-sectional side-view in FIG. 8. The cross-sectional view in FIG. 8 is taken along cut line B—B of FIG. 7. A thicker or so-called "maxi" napkin, suitable for use by a woman during days of higher menstrual flow, is depicted in schematic cross-sectional side view in FIG. 9 where the napkin includes a super-absorbent pleget, 94 in addition to the same elements as the mini napkin of FIG. 8.

In FIG. 8, the elements of the napkin, shown in plan view, are built up from the lowest garment-side "barrier component" to the uppermost body-side "cover" component of the napkin. The cover component of the napkin, made of a material of a type well known in the art, is permeable to body fluids and is the component of the napkin worn closest to the user's body during use. The barrier component, also made of materials of a type well known in the art, is of an impermeable material and is worn furthest from the user's body, next to the undergarments.

Figure 9:
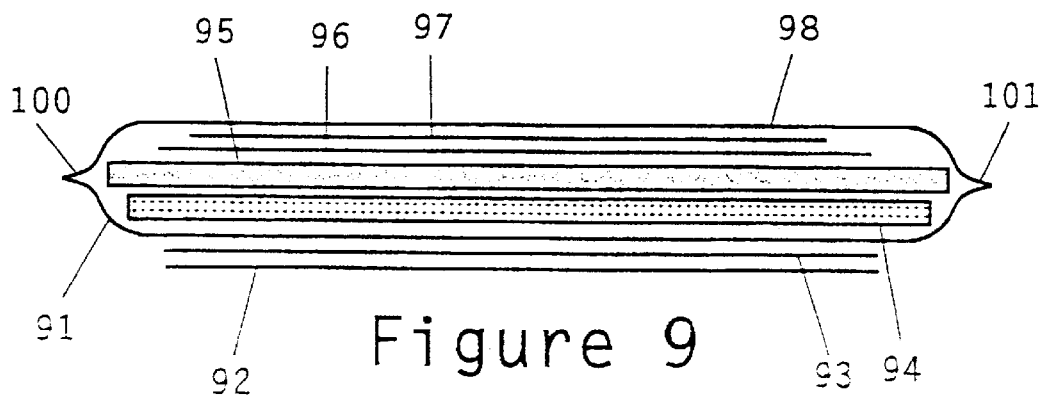
FIG. 9 is a cut-away side view of a so-called "maxi" sanitary napkin as in FIG. 8, showing the additional component of a super-absorbent pleget 94.

The napkin 90 depicted in FIG. 7, 8, or 9 and described in this Example comprises a unique distribution feature which serves to disseminate, or distribute, body fluids prior to their reaching the absorbent component of the napkin in order to provide a more efficient napkin having longer service life prior to the need for its replacement and resulting greater comfort to the user. The distribution feature includes distribution and delay components not found in prior art napkins. The specific materials used for the various components of the napkin are described in detail in co-pending application Serial No. (Attorney's Docket No. 13303.10), the contents of which are incorporated herein by reference.

In the napkin shown in FIGS. 7–9, the cover layer 98 corresponds to the first web of material described in the general process detailed above. The distribution layer component 97 corresponds to the first cut component, and the transfer delay component 96 corresponds to the second cut workpiece component. The barrier layer 91 corresponds to the web of fourth material, and absorbent layers 95 and 94, adhesive strip 93 and adhesive peel strip 92 correspond to elements attached to the barrier layer 91 in process steps not part of this invention.

In this Example, specific lengths of the napkin and each component will be given to aid in understanding the invention. However, it is to be understood that the specific dimensions are cited merely for illustrative purposes and should not be read as limiting the scope of the invention as it is defined by the appended claims.

Referring to FIG. 8, the napkin 90 has, when finally cut along dashed cut line 102, a dog-bone shape and an overall length $L_p$ equal to about 300 mm. With, for example, an allowance for in-process strain of 2 percent and a scrap of 3 mm between successive finished napkins when they are cut along dashed line 102, the product repeat length $L_{PR}$ is 306 mm. The napkin 90 comprises an upper cover layer 98 which is permeable to body fluids. Cover 98 constitutes the moving web of material 71 mentioned in the general process discussion above.

Directly under the cover layer 98 there is a distribution component 97 of length, $L_{C2}$, about 254 mm and component repeat length, $L_{CR2}$, of about 260 mm fabricated of a material which serves as a wicking agent to aid in the more or less uniform distribution of body fluids to the absorbent component below.

Directly under the distribution component 97 there is a transfer delay component 96 of length, $L_{C1}$, about 268 mm and component repeat length, $L_{CR1}$, of about 275 mm which is somewhat less permeable to body fluids than the cover layer 98. Transfer delay component 96 acts to slightly retard the flow of body fluids to permit the distribution component 97 above to effectively carry out its wicking function prior to the passage of body fluids through to the absorbent component 95 below. Lying under the absorbent layer 95 in the mini napkin of FIGS. 8 and 9 is the fluid impermeable garment-side or barrier layer 91.

In the maxi napkin of FIG. 9 the same elements, bearing the same reference numerals, are also present, however, a super-absorbent pleget component 94 is shown interposed between the absorbent layer 95 and the barrier layer 91. Both the mini and maxi napkins of FIGS. 8 and 10 are shown with the upper cover layer 98 sealed to the lower barrier layer 91 by seals 100 and 101 in the conventional manner. Also conventional garment adhesive strip 93 and protective adhesive peel strip 92 are shown for both napkins.

Referring again to FIGS. 7, 8, and 9, under the transfer delay component 96 there is the absorbent component 95. The barrier component 91, laying under the absorbent component 95, is typically made of a polymeric material which is not permeable to body fluids and which serves to shield the user's undergarments from staining by body fluids.

In the napkin 90 depicted in FIG. 7, the cover component is generally translucent and is typically made of a white material. To provide the consumer with visual cues that the napkin being purchased has the distribution feature mentioned above, the absorbent layer 95, transfer delay component 96 and distribution component 97 are fabricated of materials of different colors. For example, the absorbent component 95 and distribution component 97 may be white, while the transfer delay component 96 may be light blue, pink, peach, or some other pleasing color. The various components, viewed through the preferably translucent cover component 98 thus form a pleasing pattern. The cross-hatched region of the transfer delay component 96 in FIG. 7 appears as a uniform band of color through the translucent upper cover component 98. To add to the visual cues, the finished napkin 90 may be further embossed with a visual cue pattern 99.

It is highly desirable that the distribution component 97 and the transfer delay component 96 be carefully registered with respect to one another, and with the optional embossed visual cue 99. If the distribution component 97 and transfer delay component 96 are mismatched, the colored band is seen as a non-uniform band and detracts from the overall aesthetic appearance of the finished product. Moreover, if the optional embossed visual cue pattern 99 is similarly mismatched with the band of color, the overall pleasing appearance of the product is diminished.

Referring to the specific components with exemplary dimensions given above, the details of the general process for making the feminine napkin of this invention become clear with reference to FIGS. 3 and 4.

A web of cover material 71 for the napkin 90 is fed to the machine of the invention at a constant speed of $L_P$ per repeat or 306 mm/repeat. A web of first component material 51 from which the distribution layer components are cut is fed to the pair of die cut and anvil rollers 22 and 24 at a constant speed of $L_{CR1}$ per repeat, or 260 mm/repeat. A web 61 of second material is fed to anvil and die cut rollers 32 and 34 at a constant linear speed of $L_{CR2}$ per repeat, or 275 mm/repeat, to be cut into distribution components.

Once the distribution layer component 53 is cut free from web 51, component 53 is fed onto the web 61 of transfer delay material, and the web 61 is cut with the first component overlaying the second in the manner detailed above.

When the second component (63 in FIG. 4), and its overlying first component (55 in FIG. 4) are free of web 61, the components 55 and 63 are transferred to web 71.

As shown in FIGS. 3 and 4, embossing and anvil rollers 42 and 44 apply an optional embossed visual cue pattern 99 to the partially finished napkin.

While there have been shown and exemplified preferred embodiments of the process and machine of the present invention, it will be clear to those skilled in the art that various departures may be made from the preferred embodiments of both the machine and process without departing from the scope of the invention as defined by the appended claims.

What is claimed is:

1. A process for manufacturing a multi-component product comprising at least two components cut from moving webs of material, registering the components with respect to one another, and depositing the registered components on a web of moving material, said components having respective leading and trailing edges, a longitudinal center line, and a longitudinal center defined by a point midway on said longitudinal center line between said leading and trailing edges, said process comprising the steps of:
   a) cutting on a first die cut and transfer apparatus a first workpiece component from a first web of material moving at first speed;
   b) directly transferring the cut first workpiece component from a first die cut and transfer apparatus to overly a web of a second material on a second die cut and transfer apparatus positioned adjacent the first die cut and transfer apparatus and moving at a second speed;
   c) cutting on the second die cut roller a second workpiece component from the second web so that the first cut component overlies the cut second component; and
   d) transferring the cut first and second workpiece components to a third web of material moving at a third speed.

2. The process of claim 1 further comprising the step of adjusting the registration of the longitudinal center of said first cut component with respect to that of said second component prior to cutting said second component from said second web of material.

3. A process according to claim 2 wherein the longitudinal centers of said first and said second workpiece components substantially coincide when the second workpiece component is cut from the second web.

4. The process of claim 2 wherein said step of adjusting the registration of the longitudinal center of said first cut component with respect to that of said second component comprises adjusting the rotational phase angle of a die cut roller cutting at least one of said first and second components from the respective first and second webs of material.

5. The process according to claim 1, 2 or 3 wherein said first workpiece component is of a length less than that of said second workpiece component.

6. A process according to claim 1, 2, or 3 wherein said first workpiece component has lateral dimensions that are less than lateral dimensions of said second workpiece component.

7. The process of claim 1 further comprising the step of embossing a pattern in the first and second cut components between step c) of cutting the second workpiece component and step d) of transferring the cut first and second workpiece components to the third web of material.

8. A process for manufacturing a multi-component product comprising at least two components cut from respective first and second moving webs of material, registering the components with respect to one another, and depositing the registered components on a third moving web of material, said components having respective leading and trailing edges, lengths between said leading and trailing edges, a longitudinal center line, and a longitudinal center defined by a point midway on said longitudinal center line between said leading and trailing edges, said process comprising the steps of:
   a) cutting on a first die cut and transfer apparatus a first workpiece component from a web of first material moving at a first speed;
   b) directly transferring the cut first workpiece component from a first die cut and transfer apparatus overlay a web of a second material on a second die cut and transfer apparatus positioned adjacent the first die cut and transfer apparatus and moving at a second speed;
   c) registering the cut first workpiece component with respect to the web of second material such that when the second workpiece component is cut from the second web of material, the longitudinal centers of the first and said second workpiece components substantially coincide;

d) cutting the second workpiece component from the second web while incorporating the overlying cut first workpiece component wholly within the cut boundaries of the second workpiece component; and e) transferring the cut first and second workpiece components to a third web of material moving at a third speed.

9. The process according to claim 8 wherein the length of said first workpiece component is less than that of said second workplace component.

10. The process according to claim 8 wherein said first workpiece component are less than those of said second workpiece component.

11. The process according to claims 8 wherein the length and lateral dimensions of said first workpiece component are less than the length and lateral dimensions of said second workplace component.

12. The process according to claim 11 wherein the longitudinal centers of said first and second workpiece components are adjusted with respect to one another whereby said first cut workpiece component lies wholly with the boundaries of said second workplace component.

13. The process according to claim 12 wherein said first and said second workpiece components are of similar shapes.

14. The process according to claim 13 wherein the longitudinal centers of said first and said second workplace components substantially coincide when said second workplace component is cut from said second web whereby the periphery of said second workpiece component protrudes from said first workpiece component in a uniform band.

15. The process according to claim 8 further comprising the step of embossing a pattern in said first and second workpiece components as said components overly said third web of material;

the first and second workpiece components between step c) of cutting the second workpiece component and step d) of transferring the cut first and second workpiece components to the third web of material.

16. The process according to claim 14 further comprising the step of embossing a pattern in said first and second workpiece components as said components overly said third web of material.

17. The process according to claim 16 wherein said pattern is substantially centered on the longitudinal center of said second workpiece component.

18. A process for manufacturing a multi-component product comprising at least two components cut from moving webs of material, registering the components with respect to one another, and depositing the registered components on a web of moving material, said components having respective leading and trailing edges, a longitudinal center line, and a longitudinal center defined by a point midway on said longitudinal center line between said leading and trailing edges, said process comprising the steps of a) cutting on a first die cut and transfer apparatus a first workpiece component from a first web of material moving at first speed;

b) directly transferring the cut first workpiece component from the first die cut and transfer apparatus to overly a web of a second material on a second die cut and transfer apparatus positioned adjacent the first die cut and transfer apparatus and moving at a second speed;

c) adjusting the longitudinal center of said cut first workpiece component with respect to the longitudinal center of said second workpiece component prior to cutting said second workpiece component from said second web of material;

d) cutting on the second die cut roller a second workpiece component from the second web so that the first cut component overlies the cut second component; and e) transferring the cut first and second workpiece components to a third web of material moving at a third speed.

19. The process according to claim 18 wherein said respective longitudinal centers of said first and said second workpiece components are adjusted to substantially coincide.

20. The process according to claim 19 wherein said first workpiece component lies wholly within the boundaries of said second workplace component.

21. The process of claim 20 further comprising the step of embossing a pattern in said cut first and second workpiece components as they overly said third web of material.

22. A process for producing a sanitary napkin comprising a cover layer permeable to body fluids, a body fluid distribution layer component lying next adjacent the cover layer, and a body fluid transfer delay layer component lying next adjacent the distribution layer component, the process comprising the steps of:

a) cutting on a first die cut and transfer apparatus the body fluid distribution component from a first web of material moving at a first speed;

b) directly transferring the body fluid distribution component from a first die cut and transfer apparatus to overlay a web of body fluid transfer delay material on a second die cut and transfer apparatus positioned adjacent the first die cut and transfer apparatus and moving at a second speed;

c) cutting the body fluid transfer delay component from the web of body fluid transfer delay material while the body fluid distribution component overlies the body fluid transfer delay component; and d) transferring the cut body fluid distribution component and body fluid transfer delay component to a web of cover material moving at a third speed.

23. The process according to claim 22 further comprising the step of adjusting the longitudinal centers of said body fluid distribution component and said body fluid transfer delay component prior to cutting the body fluid transfer delay component from the web of body fluid transfer delay material.

24. The process according to claim 23 wherein the longitudinal centers of said body fluid distribution component and said body fluid delay component are adjusted to substantially coincide.

25. The process according to claim 24 wherein said body fluid distribution component and said body fluid transfer delay component are of similar shapes.

26. The process according to claim 25 wherein dimensions of said body fluid distribution component are less than dimensions of said body fluid transfer delay component whereby peripheral edges of said body fluid transfer delay component protrude around the periphery of said body fluid distribution component to provide a uniform band.

27. The process of claim 26 wherein said cover material is of a translucent material whereby said protruding band of said body fluid transfer delay component is visible through said cover layer.

28. The process of claim 27 wherein said fluid transfer delay component material is of a color different from said cover layer material and said body fluid distribution material whereby said visible band is of said color.

29. The process according to claim 22 further comprising the step of embossing a pattern in said body fluid distribution component and said body fluid transfer delay component as they overly said web of cover material.

30. The process according to claim 29 wherein the longitudinal centers of said body fluid distribution component and said body fluid distribution component and said body fluid transfer delay component are adjusted to substantially coincide prior to cutting said body fluid distribution component and said body fluid transfer delay component from said web of body fluid transfer delay material.

31. The process of claim 30 wherein the pattern embossed is substantially centered on said body fluid distribution component and said body fluid distribution component and said body fluid transfer delay component.

* * * * *